United States Patent
Tizard et al.

(10) Patent No.: US 10,815,502 B2
(45) Date of Patent: Oct. 27, 2020

(54) CARBON CAPTURE IN FERMENTATION

(71) Applicant: LanzaTech New Zealand Limited, Skokie, IL (US)

(72) Inventors: Joseph Henry Tizard, Skokie, IL (US); Paul Alvin Sechrist, Skokie, IL (US)

(73) Assignee: LANZATECH NEW ZEALAND LIMITED, Skokie, IL (US)

(*) Notice: Subject to any disclaimer, the term of this patent is extended or adjusted under 35 U.S.C. 154(b) by 425 days.

(21) Appl. No.: 14/516,564

(22) Filed: Oct. 16, 2014

(65) Prior Publication Data

US 2015/0111266 A1  Apr. 23, 2015

Related U.S. Application Data

(60) Provisional application No. 61/892,405, filed on Oct. 17, 2013.

(51) Int. Cl.
- *C12P 7/18* (2006.01)
- *C12P 7/06* (2006.01)
- *C12P 7/08* (2006.01)
- *C12P 7/54* (2006.01)

(52) U.S. Cl.
CPC ............... *C12P 7/18* (2013.01); *C12P 7/065* (2013.01); *C12P 7/08* (2013.01); *C12P 7/54* (2013.01); *Y02E 50/17* (2013.01)

(58) Field of Classification Search
None
See application file for complete search history.

(56) References Cited

U.S. PATENT DOCUMENTS

| | | |
|---|---|---|
| 5,173,429 A | 12/1992 | Gaddy et al. |
| 5,593,886 A | 1/1997 | Gaddy |
| 5,807,722 A | 9/1998 | Gaddy |
| 5,821,111 A | 10/1998 | Grady et al. |
| 6,136,577 A | 10/2000 | Gaddy |
| 6,340,581 B1 | 1/2002 | Gaddy |
| 6,368,819 B1 | 4/2002 | Gaddy et al. |
| 8,143,037 B2 | 3/2012 | Zahn et al. |
| 8,263,372 B2 | 9/2012 | Oakley |
| 8,383,376 B2 | 2/2013 | Simpson et al. |

(Continued)

FOREIGN PATENT DOCUMENTS

| | | |
|---|---|---|
| WO | WO2002/08438 | 1/2002 |
| WO | WO2007/117157 | 10/2007 |

(Continued)

OTHER PUBLICATIONS

Abrini, J. Naveau, H. & Nyns, E. J., Archives of Microbiology, (1994), 161, 345-351.

(Continued)

*Primary Examiner* — Robert J Yamasaki
*Assistant Examiner* — Charles Zoltan Constantine
(74) *Attorney, Agent, or Firm* — Frank S. Molinaro

(57) ABSTRACT

The invention provides processes and methods for utilization of carbon dioxide ($CO_2$) in the fermentation of a gaseous substrate comprising hydrogen ($H_2$) and $CO_2$. In particular, the invention allows for the conversion of at least a portion of the $CO_2$ in the gaseous substrate to one or more products, such as ethanol, acetate, and/or 2,3-butanediol.

16 Claims, 5 Drawing Sheets

(56) References Cited

U.S. PATENT DOCUMENTS

| | | | |
|---|---|---|---|
| 2003/0211585 A1* | 11/2003 | Gaddy | C12P 7/065 |
| | | | 435/161 |
| 2011/0236919 A1 | 9/2011 | Zahn | |
| 2011/0269197 A1* | 11/2011 | Barker | C12M 35/02 |
| | | | 435/136 |
| 2012/0045807 A1 | 2/2012 | Simpson et al. | |
| 2012/0156739 A1* | 6/2012 | Schultz | C01B 3/025 |
| | | | 435/140 |

FOREIGN PATENT DOCUMENTS

| WO | WO2008/028055 | 3/2008 |
|---|---|---|
| WO | WO2009/064200 | 5/2008 |
| WO | 2013/119866 A1 | 8/2013 |
| WO | 2013119866 A1 | 8/2013 |

OTHER PUBLICATIONS

Hensirisak P., et al., Scale-Up Microbubble Dispersion Generator for Aerobic Fermenation, Appl Biochem Biotechnol, (2002), 101, pp. 211-227.

Klasson K. T. et al., Bioconversion of synthesis gas into liquid or gaseous fuels, Enzyme and Microbial Technology, (1992), 14, 602-608.

Klasson K. T. et al., Bioreactors for synthesis gas fermentations resources, Conservation and Recycling, (1991), 5, 145-165.

Klasson, K. T. et al., Bioreactor design for synthesis gas fermentations, Fuel, (1991), 70, 605-614.

Kopke, M., et al., Fermentative production of ethanol from carbon monoxide, Current Opinion in Biotechnology, (2011), 22, pp. 320-325.

Perez, J.M., et al., Biocatalytic reduction of short-chain carboxylic acids into their corresponding alchols with syngas fermetation, Biotechnology and Bioengineering, (2012), 110, pp. 1066-1077.

Tanner, R. S. Miller, L. M., & Yang, D., International Journal of Systematic Bacteriology, (1993), 43, 232-236.

Vega, J. L. et al., Design of Bioreactors for Coal Synthesis Gas Fermentations, Resources, Conservation and Recycling, (1990), 3. 149-160.

Vega, J. L., et al., Study of gaseous substrate fermentations: Carbon monoxide conversion to acetate. 1. Batch culture, Biotechnology and Bioengineering, (1989), 34. 6. 774-784.

PCT Search Report (PCT/US2014/060980) dated Jan. 12, 2015.

Spath P.L. et al., Preliminary Screening—Technical and Economic Assessment of Synthesis Gas to Fuels and Chemicals with Emphasis on the Potential for Biomass Derived Syngas, National Renewable Energy Laboratory Technical Report, Dec. 2003.

Office Action for Eurasian Patent Application 201690646/28, The Eurasian Patent Office, dated Aug. 23, 2017.

Examination Report for European Patent Application 14853873.9, European Patent Office, dated Mar. 23, 2018.

Office Action for Patent Application 2016-522808, Japanese Intellectual Property Office, dated Aug. 14, 2018.

Cotter, Jacqueline L., Influence of process parameters on growth of Clostridium Ijungdahii a Clostridium autoethanogenum on synthesis gas, Enzyme and Microbial Tech, 2000, pp. 281-288, vol. 44.

* cited by examiner

CARBON CAPTURE IN FERMENTATION

CROSS REFERENCE TO RELATED APPLICATIONS

This application claims the benefit of U.S. Provisional Patent Application 61/892,405 filed Oct. 17, 2013, the entirety of which is incorporated herein by reference.

FIELD OF THE INVENTION

The invention relates to the field of microbial fermentation of gases, particularly to a novel process for utilization of carbon dioxide in the anaerobic fermentation of gaseous substrates.

BACKGROUND OF THE INVENTION

Ethanol is rapidly becoming a major hydrogen-rich liquid transport fuel around the world. Consumption of ethanol in 2013 was an estimated 13.18 billion gallons in the USA alone. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

Catalytic processes may be used to convert gases consisting primarily of CO and/or $CO_2$ and $H_2$ into a variety of fuels and chemicals. Microorganisms may also be used to convert these gases into fuels and chemicals. These biological processes, although generally slower than chemical reactions, have several advantages over catalytic processes, including higher specificity, higher yields, lower energy costs and greater resistance to poisoning.

The ability of microorganisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 1998/00558, WO 2000/068407, WO 2002/008438, U.S. Pat. Nos. 5,173,429, 5,593,886, and 6,368,819. The bacterium *Clostridium autoethanogenum* is also known to produce ethanol from gases (Abrini, *Arch Microbiol*, 161: 345-351, 1994).

Studies on gas fermentation have demonstrated that CO is the dominant carbon source utilized by carboxydotrophic microorganisms for production of ethanol, while $CO_2$ is largely unutilized by the microorganisms. Accordingly, there is a strong need for improved gas fermentation processes that convert even a portion of the $CO_2$ in a gaseous substrate to useful products, such as alcohols and/or acids.

SUMMARY OF THE INVENTION

The invention provides a process for improving carbon capture in gas fermentation by providing a gaseous substrate comprising $H_2$ and $CO_2$ to a bacterial culture that converts at least a portion of the $CO_2$ in the gaseous substrate to one or more products. The invention further provides a method of producing one or more products by gas fermentation by providing a gaseous substrate comprising $H_2$ and $CO_2$ to a bacterial culture that converts at least a portion of the $CO_2$ in the gaseous substrate to one or more products. Ideally, the amount of $CO_2$ consumed by the culture exceeds or is equal to the amount of $CO_2$ produced by the culture.

The gaseous substrate may comprise CO, in addition to $H_2$ and $CO_2$. The ratio of component gasses (e.g., $H_2:CO_2$ or $H_2:CO_2:CO$) in the gaseous substrate may vary. Additionally, the ratio of the uptake or specific uptake of the component gasses (e.g., $H_2:CO_2$) in the gaseous substrate may vary. In one embodiment, the specific uptake of $H_2$ by the culture exceeds the specific uptake of CO by the culture.

The fermentation products may include, for example, alcohols and/or acids. In one embodiment, the products comprise one or more of ethanol, acetate, and 2,3-butanediol.

The bacteria may be any bacteria capable of fermenting a gaseous substrate comprising $H_2$, $CO_2$, and/or CO. The bacteria may be carboxydotrophic, such as bacteria derived from one or more of *Clostridium, Moorella, Oxobacter, Peptostreptococcus, Acetobacterium, Eubacterium,* or *Butyribacterium*. Specifically, the bacteria may comprise *Clostridium autoethanogenum* or *Clostridium ljungdahlii*, such as *Clostridium autoethanogenum* deposited under DSMZ accession number DSM23693 or bacteria derived therefrom.

The process or method may further comprise recovering one or more products.

DETAILED DESCRIPTION OF THE INVENTION

Figure 1:
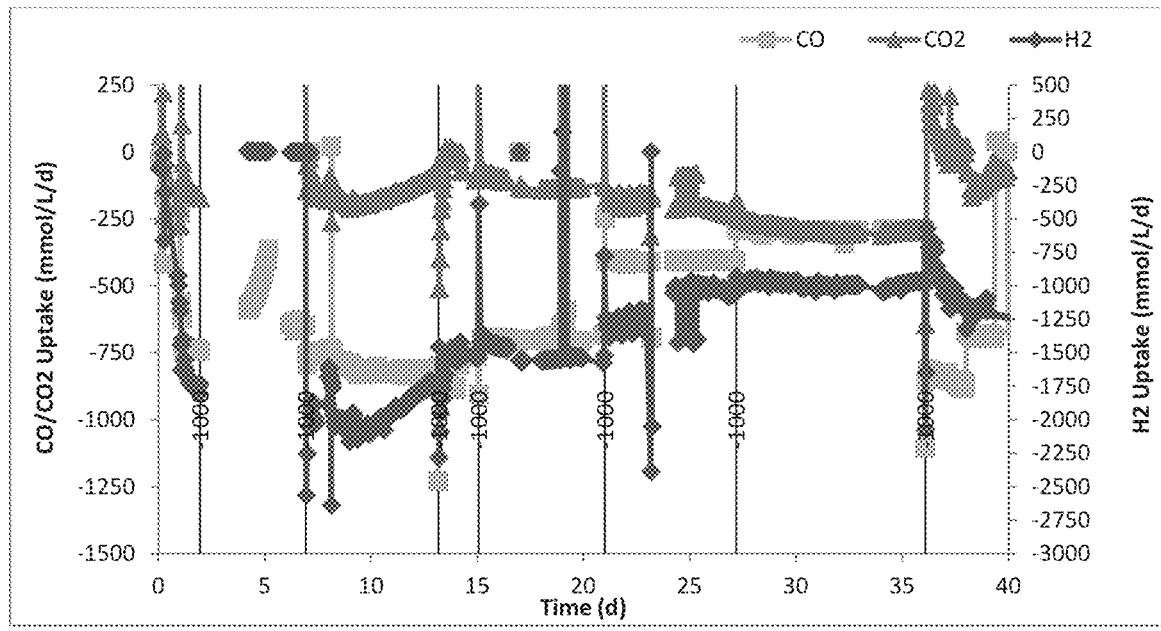
FIG. 1 is a graph showing changes in the uptake of CO, $CO_2$, and $H_2$ by a culture contained in a first reactor in response to changes in the feed gas composition.

The invention provides a process for improving carbon capture in gas fermentation by providing a gaseous substrate comprising $H_2$ and $CO_2$ to a bacterial culture that converts at least a portion of the $CO_2$ in the gaseous substrate to one or more products. The invention further provides a method of producing one or more products by gas fermentation by providing a gaseous substrate comprising $H_2$ and $CO_2$ to a bacterial culture that converts at least a portion of the $CO_2$ in the gaseous substrate to one or more products.

Anaerobic bacteria have been demonstrated to produce ethanol and acetate from $H_2$ and CO via the acetyl-CoA biochemical pathway, which may involve a number of different reactions, depending on the reaction conditions and concentrations of substrates and products. For example, acetate may be produced from the 1:1 uptake of $H_2$ and CO: $2CO+2H_2 \rightarrow CH_3COOH$. Ethanol and $CO_2$ may be produced from the 1:1 uptake of $H_2$ and CO: $3CO+3H_2 \rightarrow CH_3CH_2OH+CO_2$. Ethanol may be produced from the 2:1 uptake of $H_2$ and CO: $2CO+4H_2 \rightarrow CH_3CH_2OH+H_2O$. Acetate may be produced from consumption of CO without $H_2$: $4CO+2H_2O \rightarrow CH_3COOH+2CO_2$. Ethanol may be produced from the consumption of CO without $H_2$: $6CO+3H_2O \rightarrow CH_3CH_2OH+4CO_2$.

Additionally, anaerobic bacteria may utilize $CO_2$ to produce products. For example, acetate may be formed from the 2:1 uptake of $H_2$ and $CO_2$: $2CO_2+4H_2 \rightarrow CH_3COOH+2H_2O$. Ethanol may be formed from the 3:1 uptake of $H_2$ and $CO_2$: $2CO_2+6H_2 \rightarrow CH_3CH_2OH+3H_2O$.

$CO_2$ producing reactions, such as those involving the specific uptake of CO and $H_2$, and $CO_2$ consuming reactions may be combined to balance to zero net $CO_2$ flux:

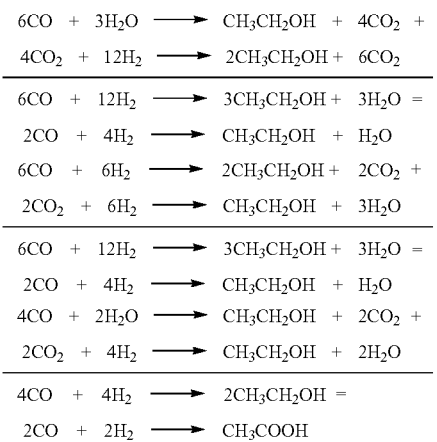

Ideally, the amount of $CO_2$ consumed by the culture exceeds or is equal to the amount of $CO_2$ produced by the culture. In other words, the fermentation may result in net carbon capture.

The gaseous substrate ("gas" or "feed gas" or "fermentation gas" or "substrate") may be any gas which contains a compound or element used by a microorganism as a carbon and/or energy source in fermentation. The gaseous substrate will typically contain a significant proportion of $H_2$, $CO_2$, and/or CO, and may additionally contain $N_2$ or other gasses. In a preferred embodiment, the gaseous substrate comprises $H_2$ and $CO_2$, but not CO. In another preferred embodiment, the gaseous substrate comprises $H_2$, $CO_2$, and CO. In anaerobic fermentation, the gaseous substrate is typically free or substantially free of $O_2$.

The composition of the gaseous substrate may vary. In particular, the ratios of $H_2$, $CO_2$, and/or CO in the gaseous substrate may vary. For example, the ratio to $H_2$:CO in the gaseous substrate may be at least 0.1:1, at least 0.5:1, at least 1:1, at least 1.5:1, at least 2:1, at least 3:1, at least 5:1 or at least 10:1. The gaseous substrate may comprise, for example, 5-40% $CO_2$, 10-25% $CO_2$, 20-50% $CO_2$, or 30-60% $CO_2$. The gaseous substrate may comprise CO and $CO_2$, for example, at a ratio of 1:1. The amount of $CO_2$ in the gaseous substrate may be 1.5-4 times the amount of CO in the gaseous substrate.

The gaseous substrate may comprise or be adjusted to comprise an excess of $H_2$. For example, the gaseous substrate may comprise about 30-90% $H_2$ or about 60-90% $H_2$. The gaseous substrate may contain a substantially higher volume of $H_2$ than $CO_2$ and CO. For example, the ratio of $H_2$:$CO_2$:CO in the gaseous substrate may be at least 2:1:1, or at least 3:1:1, or at least 5:1:1. The amount of $H_2$ in the gaseous substrate may be 1.5-5 times the amount of CO in the gaseous substrate. A gas stream or gas source may be supplemented with $H_2$ (or $CO_2$ or CO) to obtain a gaseous substrate with a desired composition.

The gaseous substrate may be sourced from an industrial process. In particular, the gaseous substrate may be a waste gas generated by an industrial process, such as ferrous metal product manufacturing (e.g., steel manufacturing), non-ferrous product manufacturing, petroleum refining, coal gasification, electric power production, carbon black production, ammonia production, methanol production, or coke manufacturing. In a preferred embodiment, the gaseous substrate is derived from a steel manufacturing gas.

The gaseous substrate may be sourced from the gasification of organic matter such as methane, ethane, propane, coal, natural gas, crude oil, low value residues from oil refinery (including petroleum coke or petcoke), solid municipal waste, or biomass. Biomass includes by-products obtained during the extraction and processing of foodstuffs, such as sugar from sugarcane, or starch from maize or grains, or non-food biomass waste generated by the forestry industry. Any of these carbonaceous materials may be gasified, i.e., partially combusted with oxygen, to produce synthesis gas (syngas). Syngas typically comprises mainly CO, $H_2$, and/or $CO_2$ and may additionally contain amounts of methane, ethylene, ethane, or other gasses. The operating conditions of the gasifier can be adjusted to provide a substrate stream with a desirable composition for fermentation or blending with one or more other streams to provide an optimised or desirable composition for increased alcohol productivity and/or overall carbon capture in a fermentation process.

The gaseous substrate may be sourced from a pressure swing adsorption (PSA) system. For example, a PSA tail gas may contain ~10-12% of the $H_2$ entering the PSA from a methane steam reformer, in addition to CO and $CO_2$ from the water-gas shift reactors in the methane steam reformer. CO in a gas exiting a primary methane reformer (at about $3H_2/CO$) may be reacted with water to form $H_2$ and $CO_2$ using water-gas shift reactors (high temperature and low temperature). The reaction conditions may be tailored to control the amount of CO present in the PSA tail gas relative to the amount of $CO_2$ present in the PSA tail gas. It may also be desirable to allow some of the $H_2$ to remain in the PSA tail gas, or to add $H_2$ back to the PSA tail gas, to achieve a desirable $H_2/CO/CO_2$ ratio. For example, the $H_2$:CO ratio may be about 2:1 and/or the $H_2$:$CO_2$ ratio may be about 3:1. Typically, the PSA will make very high purity $H_2$ product. The recovery of $H_2$ is mainly affected by the feed gas pressure to tail gas pressure ratio. Running the tail gas at the minimum pressure gives the highest $H_2$ recovery. Since the tail gas is usually sent to the fuel gas header (to be used anywhere in the refinery), it may be at a pressure of ~15 psig. If it is burned in dedicated burners in the primary reformer, it may be at a pressure as low as 5 psig. If PSA tail gas is used as a feed gas source for a fermenter, the pressure of the tail gas may be adjusted to 30-45 psig to avoid the need for gas compression.

The gaseous substrate may be directed, in whole or in part, to a fermentation by any suitable conduit means. For example, piping or other transfer means may be connected to the waste gas stack from a steel mill to divert at least a portion of the waste gas to a fermentation system. One or more fans may be used to divert at least a portion of the waste gas into the fermentation system. While steel mills can be adapted to substantially continuously produce steel (and subsequently waste gases), particular aspects of the process may be intermittent. Typically, the decarburisation of steel is a batch process lasting several minutes to several hours. A conduit means may be adapted to divert at least a portion of the waste gas to the fermentation system if it is determined the waste gas has a desirable composition.

It may be desirable to filter, scrub, or otherwise pre-treat the gaseous substrate before it is used in fermentation to remove chemical or physical impurities or contaminants. For example, source gasses may be passed through water or otherwise filtered to remove particulate matter, long chain hydrocarbons, or tars. However, such filtration or pre-treatment is not always required. It is sometimes possible to provide unfiltered, untreated gaseous substrate directly to the fermentation culture.

The composition of the gaseous substrate may be altered to improve fermentation efficiency, product production, and/or overall carbon capture. In particular, the gaseous substrate may be altered to contain a higher or lower amount of $H_2$, $CO_2$, and/or CO by combining or blending streams from two or more sources. For example, a stream comprising a high concentration of $CO_2$, such as the exhaust from a steel mill converter, may be combined or blended with a stream comprising high concentrations of $H_2$ and CO, such as the off-gas from a steel mill coke oven. Alternatively or additionally, an intermittent stream comprising $CO_2$, such as an exhaust stream from a steel mill converter, may be combined or blended with a substantially continuous stream comprising CO, $CO_2$, and $H_2$, such as syngas produced in a gasification process. For example, a stream produced by a gasifier may be increased and/or decreased in accordance with the intermittent production of $CO_2$ from an industrial source in order to maintain a substantially continuous substrate stream with a desirable or optimised composition.

The substrate streams will typically be gaseous, but may also be liquid or solid. For example, $CO_2$ may be provided to a reactor as a liquid or as a $CO_2$-saturated liquid. By way of example, a microbubble dispersion generator, such as that described in Hensirisak, *Appl Biochem Biotechnol*, 101: 211-227, 2002) may be used.

Gas fermentation is a metabolic process by which a gaseous substrate is used as a carbon and/or energy source for the production of ethanol or other products or chemicals. As used herein, the term "fermentation" encompasses both the growth phase and the product biosynthesis phase of the process. The gas fermentation is performed by a microorganism, typically bacteria.

The bacteria may be any bacteria capable of fermenting a gaseous substrate comprising $H_2$, $CO_2$, and/or CO. The bacteria may be carboxydotrophic, such as bacteria derived from *Clostridium*, *Moorella*, *Oxobacter*, *Peptostreptococcus*, *Acetobacterium*, *Eubacterium*, or *Butyribacterium*. In particular, the bacteria may be *Clostridium autoethanogenum*, *Clostridium ljungdahli*, *Clostridium carboxidivorans*, *Clostridium drakei*, *Clostridium scatologenes*, *Clostridium aceticum*, *Clostridium formicoaceticum*, *Clostridium magnum*, *Butyribacterium methylotrphoicum*, *Acetobacterium woodii*, *Alkalibaculum bacchi*, *Blautia producta*, *Eubacterium limosum*, *Moorella thermoacetica*, *Sporomusa ovata*, *Sporomusa silvacetica*, *Sporomusa sphaeroides*, *Oxobacter pfennigii* and *Thermoanaerobacter kiuvi*. The bacteria may also be a strain derived from any of the aforementioned genus or species.

The bacteria may be derived from the cluster of carboxydotrophic *Clostridia* comprising the species *C. autoethanogenum*, *C. ljungdahlii*, *C. ragsdalei*, and related isolates. These include but are not limited to strains *C. autoethanogenum* JAI-1T (DSM10061) (Abrini, *Arch Microbiol*, 161: 345-351, 1994), *C. autoethanogenum* LBS1560 (DSM19630) (WO 2009/064200), *C. autoethanogenum* LBS1561 (DSM23693), *C. ljungdahlii* PETCT (DSM13528=ATCC 55383) (Tanner, *Int J Syst Bacteriol*, 43: 232-236, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* 0-52 (ATCC 55989) (U.S. Pat. No. 6,368,819), *C. ragsdalei* P11T (ATCC BAA-622) (WO 2008/028055), related isolates such as "*C. coskatii*" (U.S. Publication 2011/0229947) and "*Clostridium* sp." (Berzin, *Appl Biochem Biotechnol*, 167: 338-347, 2012), or mutated strains such as *C. ljungdahlii* OTA-1 (Tirado-Acevedo, Production of Bioethanol from Synthesis Gas Using *Clostridium ljungdahlii*, PhD thesis, North Carolina State University, 2010). These strains form a subcluster within the *Clostridial* rRNA cluster I, and their 16S rRNA gene is more than 99% identical with a similar low GC content of around 30%. However, DNA-DNA reassociation and DNA fingerprinting experiments showed that these strains belong to distinct species (WO 2008/028055).

All species of the above-referenced cluster have a similar morphology and size (logarithmic growing cells are between 0.5–0.7×3-5 μm), are mesophilic (optimal growth temperature between 30-37° C.), and strictly anaerobic (Abrini, *Arch Microbiol*, 161: 345-351, 1994; Tanner, *Int J Syst Bacteriol*, 43: 232-236, 1993; and WO 2008/028055). Moreover, they all share the same major phylogenetic traits, such as same pH range (pH 4-7.5, with an optimal initial pH of 5.5-6), strong autotrophic growth on CO-containing gases with similar growth rates, and a similar metabolic profile with ethanol and acetic acid as main fermentation end product, and small amounts of 2,3-butanediol and lactic acid formed under certain conditions (Abrini, Arch Microbiol, 161: 345-351, 1994; Köpke, Curr Opin Biotechnol, 22: 320-325, 2011; Tanner, Int J Syst Bacteriol, 43: 232-236, 1993; and WO 2008/028055). Indole production was observed with all three species as well. However, the species differentiate in substrate utilization of various sugars (e.g. rhamnose, arabinose), acids (e.g. gluconate, citrate), amino acids (e.g. arginine, histidine), or other substrates (e.g. betaine, butanol). Moreover some of the species were found to be auxotrophic to certain vitamins (e.g. thiamine, biotin) while others were not. The organization and number of Wood-Ljungdahl pathway genes, responsible for gas uptake, has been found to be the same in all species, despite differences in nucleic and amino acid sequences (Köpke, Curr Opin Biotechnol, 22: 320-325, 2011). Also reduction of carboxylic acids into their corresponding alcohols has been shown in a range of these microorganisms (Perez, Biotechnol Bioeng, 110:1066-1077, 2012). These traits are therefore not specific to one organism like *C. autoethanogenum* or *C. ljungdahlii*, but rather general traits for carboxydotrophic, ethanol-synthesizing Clostridia and it can be anticipated that mechanisms work similarly across these strains, although there may be differences in performance (Perez, Biotechnol Bioeng, 110:1066-1077, 2012).

In a preferred embodiment, the bacteria is *Clostridium autoethanogenum* or *Clostridium ljungdahlii*. In another embodiment, the bacteria is *Clostridium autoethanogenum* having the identifying characteristics of the strains deposited under the German Resource Centre for Biological Material (DSMZ) accession number DSM10061 or DSM23693. In a further preferred embodiment, the bacteria is *Clostridium autoethanogenum* deposited under DSMZ accession number DSM10061 or DSM23693 or a bacteria derived from the *Clostridium autoethanogenum* deposited under DSMZ accession number DSM10061 or DSM23693.

The uptake ("consumption") and specific uptake ("specific consumption") of the gaseous substrate by the bacterial culture may vary. Uptake is generally described in terms of unit of component gas (e.g., mmol of $H_2$, $CO_2$, or CO) consumed by unit of fermentation broth (e.g., L of fermentation broth) per unit time (e.g., day), for example mmol/L/day. The culture may uptake, for example, at least 1000 mmol/L/day of $H_2$, at least 2000 mmol/L/day of $H_2$, at least 4000 mmol/L/day of $H_2$, or at least 6000 mmol/L/day of $H_2$. Additionally, the culture may uptake, for example, at least 500 mmol/L/day of $CO_2$, at least 1000 mmol/L/day of $CO_2$, at least 2000 mmol/L/day of $CO_2$, or at least 3000 mmol/L/day of $CO_2$. Specific uptake is generally described in terms of unit of component gas (e.g., mmol of $H_2$, $CO_2$, or CO) consumed by unit of microorganism (e.g., gram of bacterial cells) per unit time (e.g., min), for example mmol/g/min. In a preferred embodiment, the specific uptake of $H_2$ by the culture exceeds the specific uptake of CO by the culture. For example, the specific uptake ratio of $H_2$:CO by the culture may be at least 1.1:1, at least 1.4:1, at least 1.6:1, at least 2:1, at least 3.1, at least 5:1, or at least 10:1.

$H_2$ and/or $CO_2$ uptake may be impaired when the ethanol and/or acetate concentration in the fermentation broth is high, or at least above a certain threshold. For example, $H_2$ uptake may be impaired when the acetate concentration exceeds about 10 g/L or about 20 g/L. To reduce the extent of $H_2$ uptake impairment, the products produced by the bacterial culture may be continuously removed from the reactor or fermentation broth. Sufficiently high cell density may be required to achieve efficient consumption of $H_2$ by the culture. Uptake of $CO_2$ may be inhibited by unhealthy biomass, gas oversupply, high ethanol concentration, and/or the presence of contaminants.

The bacterial culture may be grown in any liquid nutrient medium that provides sufficient resources to the culture. The liquid nutrient medium may contain, for example, vitamins, minerals, and water. Examples of suitable liquid nutrient media are known in the art, including anaerobic media suitable for the fermentation of ethanol or other products (see, e.g., U.S. Pat. Nos. 5,173,429, 5,593,886, and WO 2002/08438).

The bacterial culture may be contained in a reactor (bioreactor). The reactor may be any fermentation device having one or more vessels and/or towers or piping arrangements for the growth of a bacterial culture. The reactor may be, for example, an immobilised cell reactor, a gas-lift reactor, a bubble column reactor (BCR), a circulated loop reactor, a membrane reactor, such as a hollow fibre membrane bioreactor (HFM BR), a continuous flow stirred-tank reactor (CSTR), or a trickle bed reactor (TBR). The reactor is preferably adapted to receive a gaseous substrate comprising $H_2$, $CO_2$, and/or CO. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

Embodiments of the invention are described by way of example. However, particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around a fermentation system by any known transfer means, in certain embodiments, the substrate and/or exhaust streams are gaseous. Particular stages may be coupled by suitable conduit means or be configurable to receive or pass streams throughout a system. A pump or compressor may be provided to facilitate delivery of the streams to particular stages. Furthermore, a compressor may be used to increase the pressure of gas provided to one or more stages.

In addition, the systems or processes of the invention may optionally include means for regulating and/or controlling other parameters to improve overall efficiency of the process. One or more processors may be incorporated into the system to regulate and/or control particular parameters of the process. For example, the system may comprise a determining means to monitor the composition of substrate and/or exhaust streams. In addition, particular embodiments may include a means for controlling the delivery of substrate streams to particular stages or elements within a particular system if the determining means determines the stream has a composition suitable for a particular stage. For example, in instances where a gaseous substrate stream contains low levels of $CO_2$ or $H_2$ or high levels of $O_2$ that may be detrimental to a fermentation reaction, the substrate stream may be diverted away from the bioreactor. The system may also include means for monitoring and controlling the destination of a substrate stream and/or the flow rate, such that a stream with a desired or suitable composition may be delivered to a particular stage.

Furthermore, it may be necessary to heat or cool particular system components or substrate streams prior to or during one or more stages in the process. In such instances, any known heating or cooling means may be used. For example, heat exchangers may be employed to heat or cool the substrate streams.

Reaction conditions may be monitored and adjusted to optimize bacterial growth rate and/or product production in the reactor. The fermentation should desirably be carried out under appropriate conditions for the desired fermentation to occur (e.g., $CO_2$-to-alcohol). Such reactions conditions include pressure, temperature, gas flow rate, liquid flow rate, media pH, media redox potential, agitation rate (if using a continuous stirred tank reactor), inoculum level, substrate concentrations (to ensure that $H_2$, $CO_2$, and/or CO in the liquid phase does not become limiting), and product concentrations (to avoid product inhibition).

General methods of culturing anaerobic bacteria are well known in the art. Exemplary techniques are provided in: (i) Klasson, *Resour Consery Recycl,* 5: 145-165, 1991; (ii) Klasson, *Fuel,* 70: 605-614, 1991; (iii) Klasson, *Enzyme Microbial Technol,* 14: 602-608, 1992; (iv) Vega, *Biotech Bioeng,* 34: 785-793, 1989; (vi) Vega, *Biotech Bioeng,* 34: 774-784, 1989; (vii) Vega, *Resour Consery Recycl,* 3: 149-160, 1990. Furthermore, processes for the production of ethanol and other alcohols from gaseous substrates are well known in the art. Exemplary processes include those described, for example, in WO 2007/117157, WO 2008/115080, U.S. Pat. Nos. 6,340,581, 6,136,577, 5,593,886, 5,807,722 and 5,821,111.

The pH of the contents of the reactor may be adjusted as required. The appropriate pH will depend on the conditions required for a particular fermentation reaction, taking into account the liquid nutrition medium and the bacteria used. In a preferred embodiment involving the fermentation of a gaseous substrate containing $H_2$, $CO_2$, and CO by *Clostridium autoethanogenum*, the pH may be adjusted to approximately 4.5 to 6.5, most preferably to approximately 5 to 5.5. Further examples include a pH 5.5 to 6.5 using *Moorella thermoacetica* for the production of acetic acid, a pH 4.5 to 6.5 using *Clostridium acetobutylicum* for the production of butanol, and a pH 7 using *Carboxydothermus hygrogenaformans* for the production of hydrogen. Means for adjusting and maintaining the pH of a reactor are well known in the art. Such means may include the use of aqueous bases, such as NaOH or $NH_4OH$, and aqueous acids, such as $H_2SO_4$.

Preferably, the reactor is configured to provide enough mass transfer to allow the bacteria to access the gaseous substrate, particularly the $H_2$ in the gaseous substrate. Long gas residence times generate high gas uptake by the bacteria. In particular embodiments, the reactor is a circulated loop reactor comprising a riser segment and a downcomer segment through which the gaseous substrate and liquid nutrient media are circulated. The reactor may additionally include a wide range of suitable gas/liquid contact modules that can provide effective mass transfer. A contact module may provide a unique geometrical environment allowing gas and liquid to mix thoroughly along a set flow path, causing the entrained gas to dissolve in the liquid more uniformly. By way of example, this contact module may include, but is not limited to, a matrix of structured corrugated metal packing, random packing, sieve plates, and/or static mixers.

The mass transfer rate of the gaseous substrate to the bacterial culture may be controlled, so that the bacterial culture is supplied with gaseous substrate at or near an optimum supply rate. The mass transfer rate may be controlled by controlling the partial pressure of the gaseous substrate and/or by controlling the liquid flow rate or gas holdup. The rate of introduction of the gaseous substrate may be monitored to ensure that the concentration of $H_2$, $CO_2$, and/or CO in the liquid phase does not become limiting. In particular embodiments, the mass transfer is controlled by controlling the partial pressure of the gaseous substrate entering the reactor.

It may be preferable to perform the fermentation at elevated pressure, i.e., at a pressure higher than ambient pressure. Operating at increased pressures allows a significant increase in the rate of $H_2$, $CO_2$, and/or CO transfer from the gas phase to the liquid phase where it can be taken up by the bacteria as a carbon source for the production of products, such as ethanol. The retention time (the liquid volume in the bioreactor divided by the input gas flow rate) may be reduced when the reactor is maintained at elevated pressure rather than atmospheric pressure. Also, because a given $CO/CO_2/H_2$-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure. For example, reactors operated at 10 atmospheres of pressure need only be one tenth the volume of those operated at 1 atmosphere of pressure. The benefits of conducting a gas-to-ethanol fermentation at elevated pressures have also been described elsewhere. For example, WO 2002/08438 describes gas-to-ethanol fermentations performed under pressures of 30 psig and 75 psig, giving ethanol productivities of 150 g/L/day and 369 g/L/day respectively. However, example fermentations performed using similar media and input gas compositions at atmospheric pressure were found to produce between 10 and 20 times less ethanol per litre per day.

The bacterial culture may produce one or more products. At least a portion of the $CO_2$ in the gaseous feed stock is converted to products, such that at least a portion of the carbon in the products is derived from carbon in $CO_2$ in the gaseous substrate. For example, at least 1%, at least 5%, at least 10%, at least 15%, at least 20%, at least 30%, at least 40%, at least 50%, at least 75%, or at least 90% of the carbon in the products may be derived from carbon in $CO_2$ in the gaseous substrate. In another embodiment, the amount of $CO_2$ in the gas exiting the reactor is lower than the amount of $CO_2$ in the gas entering the reactor (i.e., lower than the amount of $CO_2$ in the gaseous substrate). For example, the amount of $CO_2$ in the gas exiting the reactor may be at least 0.5%, at least 1%, at least 3%, at least 5%, at least 10%, at least 15%, at least 20%, at least 30%, at least 40%, at least 50%, at least 75%, or at least 90% lower than the amount of $CO_2$ in the gas entering the reactor.

Products may include alcohols, acids, or other chemicals. Such products may also include gases produced by the fermentation process. In particular, the culture may produce one or more of ethanol, acetic acid (or acetate), 2,3-butanediol, butanol, isopropanol, lactate, succinate, methyl ethyl ketone (MEK), propanediol, 2-propanol, acetoin, isobutanol, citramalate, butadiene, poly lactic acid, isobutylene, 3-hydroxy propionate (3HP), acetone, and fatty acids. The inventors are the first to demonstrate high production of ethanol through consumption of $CO_2$ in gas fermentation. In a preferred embodiment, the culture produces one or more of ethanol, acetate, and 2,3-butanediol.

The culture may produce ethanol and acetate in varying amounts. For example, the culture may produce ethanol and acetate at a ratio of about 1:1. In preferred embodiments, the culture produces ethanol and acetate at a ratio of at least 1.5:1, at least 2:1, at least 3:1, or at least 5:1. The culture may produce ethanol at a concentration of at least 10 g/L or at least 15 g/L. The culture may produce acetate or acetic acid at a concentration of 20 g/L or less or 10 g/L or less.

The process or method may comprise recovering one or more products using any means known in the art. Exemplary methods are described in WO 2007/117157, WO 2008/115080, U.S. Pat. Nos. 6,340,581, 6,136,577, 5,821,111, 5,807,722 and 5,593,886.

Ethanol may be recovered from the fermentation broth, for example, by methods such as fractional distillation or evaporation or extractive fermentation. Distillation of ethanol from a fermentation broth yields an azeotropic mixture of ethanol and water (e.g., 95% ethanol and 5% water). Anhydrous ethanol can subsequently be obtained through the use of molecular sieve ethanol dehydration technology, which is well known in the art. Extractive fermentation involves the use of a water-miscible solvent that presents a low toxicity risk to the fermentation microorganism to recover the ethanol from the dilute fermentation broth. For example, oleyl alcohol may be used as a solvent in extractive fermentation. When oleyl alcohol is continuously introduced into a fermenter, it rises to form a layer at the top of the fermentation broth. This layer may then be extracted and fed through a centrifuge. Water and cells are then readily separated from the oleyl alcohol and returned to the fermenter, while the ethanol-laden solvent is fed into a flash vaporization unit. Most of the ethanol is vaporized and condensed while the non-volatile oleyl alcohol is recovered for re-use in fermentation.

Acetate may also be recovered from the fermentation broth using methods known in the art. For example, an adsorption system involving an activated charcoal filter may be used. In this case, microbial cells are typically first removed from the fermentation broth using a suitable separation method. Numerous filtration-based methods of generating a cell free fermentation broth for product recovery are known in the art. The cell-free permeate-containing ethanol and acetate—is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth be reduced to less than about 3 before it is passed through the activated charcoal column to convert the majority of the acetate to the acetic acid form.

The products of the fermentation reaction may be recovered from the fermentation broth by continuously removing a portion of the broth from the fermentation bioreactor, separating microbial cells from the broth, and recovering one or more products from the broth simultaneously or sequentially. The separated microbial cells may be returned to the fermentation reactor. The cell-free permeate remaining after the ethanol and acetate have been removed may also be returned to the fermentation reactor. Additional nutrients, such as B vitamins, may be added to replenish the cell-free permeate before it is returned to the reactor. If the pH of the broth was adjusted to enhance adsorption of acetic acid to the activated charcoal, the pH of the cell-free permeate may also need to be re-adjusted.

The reactor may be integrated with a cell recycle system that provides a means for separating bacteria from the permeate so that the bacteria may be returned to the reactor for further fermentation. A cell recycle module may continuously draws broth permeate, while retaining cells. The cell recycle system may include, but is not limited to, cell recycle membranes and disc-stack centrifugal separators.

EXAMPLES

The following examples further illustrate the invention but, of course, should not be construed to limit its scope in any way.

Example 1

This example demonstrates the preparation, inoculation, and fermentation of four bioreactors (reactors 1-4).

To a 2 L bioreactor the following components were added to make a working volume of 1.5 L; 1450 ml $H_2O$, 37.5 ml of 1M KCl, 3 ml of 1M NaCl, 3 ml of 1 M $MgCl_2$, 3 ml of 1 M $CaC_2$, 0.6 ml of 85% $H_3PO_4$, 1.5 mL resazurin (2 g/L), 7.5 ml of trace metal solution, and 30 ml B-vitamin stock solution.

| Media | Concentration (mM/L) |
|---|---|
| $MgCl_2$ 6 $H_2O$ | 2 |
| NaCl | 2 |
| $CaCl_2$ 6 $H_2O$ | 2 |
| KCl | 25 |
| $H_3PO_4$ 85% | 0.375 mL |
| Trace metal solution | 5 mL (1x) |
| B-vitamin solution | 20 mL (2x) |

| Trace metal solution | Final concentration in the media (μmol/L) 1x | Concentration (mM/L) in 200 x stock solution |
|---|---|---|
| $FeCl_2$ 4 $H_2O$ | 100 | 20 |
| $CoCl_2$ 6 $H_2O$ | 5 | 1 |
| $ZnCl_2$ | 5 | 1 |
| $H_3BO_3$ | 2 | 0.4 |
| $MnCl_2$ 4 $H_2O$ | 2 | 0.4 |
| $Na_2MoO_4$ 2 $H_2O$ | 2 | 0.4 |
| $NiCl_2$ 6 $H_2O$ | 2 | 0.4 |
| $Na_2WO_4$ 2 $H_2O$ | 2 | 0.4 |
| $Na_2SeO_3$ | 2 | 0.4 |

| B-vitamin stock solution | Final concentration in the media (mg/L) 2x | Concentration (mg/L) in 100 x stock solution |
|---|---|---|
| Thiamine hydrocloride (B1) | 1 | 50 |
| Riboflavin (B2) | 1 | 50 |
| Nicotinic acid (B3) | 1 | 50 |
| Pantothenic acid (B5) | 1 | 50 |
| Pyridoxinehydrochloride (B6) | 0.2 | 10 |
| Biotin (B7) | 0.4 | 20 |
| Folic acid (B9) | 0.2 | 10 |
| 4-Aminobenzoic acid (PABA or B10) | 1 | 50 |
| Cyanocobalamin (B12) | 1 | 50 |
| Lipoic acid (thiotic acid) | 1 | 50 |

Stirring was switched on the 300 rpm, and the reactor was heated to 37° C. $N_2$ was sparged at 200 ml/min for at least 1 hour. The inlet gas was then switched to 50 ml/min RMG at 300 rpm. $Na_2S$ drip started at 0.3 ml/hour. ORP was adjusted to be within −150 mV to −250 mV. Cr(II) was used to adjust ORP as required to maintain value within identified range. $NH_4OH$ (5M) was used as base compensation.

The reactor was then inoculated with 200 ml of an actively growing *Clostridium autoethanogenum* culture. The culture comprised *Clostridium autoethanogenum* strain DSMZ23693.

Reactors 1-4 were then fermented, as described below. The listed values are approximate, allowing ~+/−0.5% wander between GC measurements.

| Reactor 1 | | |
|---|---|---|
| Day | Notes | Gas |
| 0 | Startup feed gas composition | 56.5% $H_2$, 4.7% $N_2$, 7.63% CO, and 30.92% $CO_2$ |
| 2.0 | Hydrogen in the gas feed was swapped for nitrogen | 1.1% $H_2$, 72.6% $N_2$, 18.1% CO, and 6.0% $CO_2$ |
| 7.01 | Nitrogen in the gas feed was switched back to hydrogen | 68.4% $H_2$, 11.5% $N_2$, 21.1% CO, and 6.9% $CO_2$ |
| 15 | Media pump rate was increased to 2.4 RPM; gas feed was adjusted to replace mill gas | 59.8% $H_2$, 12.1% $N_2$, 18.2% CO, and 13.7% $CO_2$ |
| 21 | CO reduced to target CO 10% | 59.6% $H_2$, 20.6% $N_2$, 10.7% CO, and 14.1% $CO_2$ |
| 27 | CO reduced to target CO 7% | 48.1% $H_2$, 23.8% $N_2$, 7.6% CO, and 16.8% $CO_2$ |

FIG. 1 shows the amount of CO, $CO_2$, and $H_2$ consumed by the culture in reactor 1.

| Reactor 2 | | |
|---|---|---|
| Day | Notes | Gas |
| 0 | Startup feed gas composition: RMG | 3.3% $H_2$, 27.2% $N_2$, 48.8% CO, and 15.1% $CO_2$ |
| 5.2 | High hydrogen blend | 69.8% $H_2$, 9.9% $N_2$, 18.6% CO, and 6.0% $CO_2$ |
| 8.3 | | 71.3% $H_2$, 3.4% $N_2$, 6.1% CO, and 20.7% $CO_2$ |
| 12.3 | | 44.4% $H_2$, 33.3% $N_2$, 4.75% CO, and 16.5% $CO_2$ |
| 19.2 | The gas feed was changed to mill gas, the media pump was increased to 30% and the permeate bleed rate was decreased to 0.7 ml/min; the gas rate doubled from 100 to 200 ml/min | 3.2% $H_2$, 26.5% $N_2$, 50.6% CO, and 15.3% $CO_2$ |
| 22.4 | The gas rate was lowered and the gas composition was changed to comprise a ratio of 4:1 $H_2$:CO | 52.2% $H_2$, 7.3% $N_2$, 14.4% CO, 23.6% $CO_2$ |
| 27.2 | Hydrogen in the gas feed was swapped out for nitrogen | 0.9% $H_2$, 56.8% $N_2$, 13.9% CO, and 22.2% $CO_2$ |
| 29.04 | The gas feed was changed back to mill gas blend | 52.0% $H_2$, 3.2% $N_2$, 18.6% CO, and 25.7% $CO_2$ |
| 29.9 | $H_2$:CO inlet ratio was adjusted slightly | 54.6% $H_2$, 2.8% $N_2$, 16.1% CO, and 25.9% $CO_2$ |
| 33.0 | Hydrogen was switched with nitrogen | 0.36% $H_2$, 52.95% $N_2$, 16.1% CO, and 23.8% $CO_2$ |

Figure 2:
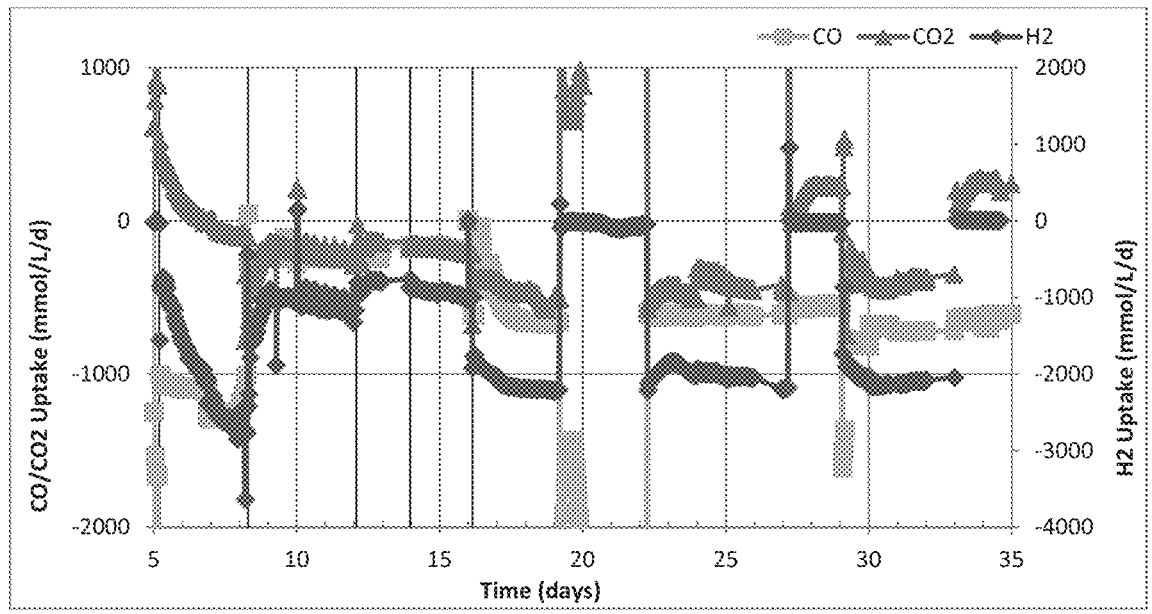
FIG. 2 is a graph showing changes in the uptake of CO, $CO_2$, and $H_2$ by a culture contained in a second reactor in response to changes in the feed gas composition.

FIG. 2 shows the amount of CO, $CO_2$, and $H_2$ consumed by the culture in reactor 2.

| Reactor 3 | | |
|---|---|---|
| Day | Notes | Gas |
| 0 | Startup feed gas composition: RMG | 3.12% $H_2$, 26.6% $N_2$, 50.5% CO, and 15.13% $CO_2$ |
| 0.18 | | 56.6% $H_2$, 2.54% $N_2$, 19.5% CO, 22.3% $CO_2$ |
| 6.0 | Hydrogen was switched with nitrogen | 0.28% $H_2$, 55.5% $N_2$, 18.6% CO, and 20.3% $CO_2$ |
| 10.9 | Nitrogen switched back with $H_2$ | 57.3% $H_2$, 2.96% $N_2$, 19.5% CO, and 22.2% $CO_2$ |
| 17.2 | | 68.1% $H_2$, 2.82% $N_2$, 19.1% CO, and 14.4% $CO_2$ |
| 19.1 | Mill gas in the gas feed was swapped out for a completely synthetic gas mixture | 59.9% $H_2$, 10.3% $N_2$, 18.9% CO, and 12.3% $CO_2$ |
| 25 | Feed gas changed to target CO 10% | 50.7% $H_2$, 20.6% $N_2$, 9.9% CO, and 15.8% $CO_2$ |
| 31.2 | Feed gas changed to target CO 7% | 49.8% $H_2$, 23.4% $N_2$ 7.1% CO, and 15.6% $CO_2$ |
| 40.1 | | 56.7% $H_2$, 4.8% $N_2$, 19.3% CO, and 14.9% $CO_2$ |

Figure 3:
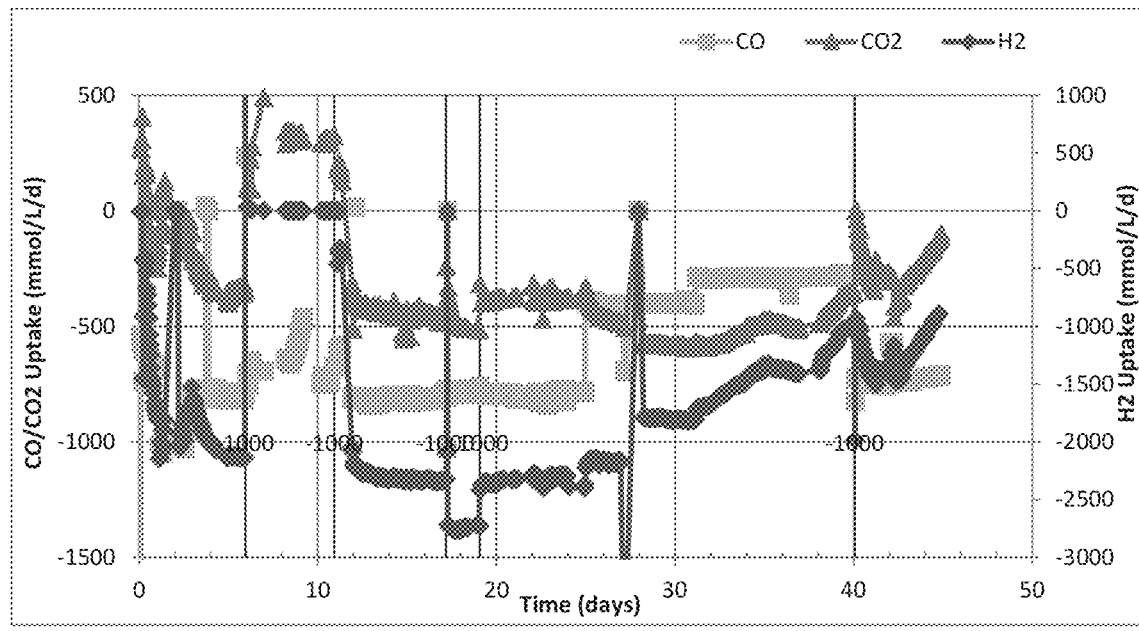
FIG. 3 is a graph showing changes in the uptake of CO, $CO_2$, and $H_2$ by a culture contained in a third reactor in response to changes in the feed gas composition.

FIG. 3 shows the amount of CO, $CO_2$, and $H_2$ consumed by the culture in reactor 3.

| Reactor 4 | | |
|---|---|---|
| Day | Notes | Gas |
| 0 | Startup feed gas composition | 55.9% $H_2$, 6.6% $N_2$, 23.2% CO, and 8.9% $CO_2$ |
| 1.1 | Continuous culture started with dilution rate of 1.18 reactor volumes per day | |
| 5.2 | Gas blend adjusted | 59.5% $H_2$, 7.2% $N_2$, 17.5% CO, and 10.2% $CO_2$ |
| 7.1 | Dilution rate reduced to 0.6 reactor volumes per day | |
| 7.94 | Media feed altered to have $1/10^{th}$ the standard quantity of molybdenum | |
| 13.2 | Molybdenum reverted back to normal concentration | |
| 15.5 | Gas blend adjusted | 51.7% $H_2$, 3.1% $N_2$, 20.2% CO, and 21.6% $CO_2$ |
| 19 | Cell recycle started, with a $D_{waste}$ of 0.06 reactor volumes per day | |
| 20 | Cell recycle relaxed to $D_{waste}$ of 0.15 reactor volumes per day | |

Figure 4:
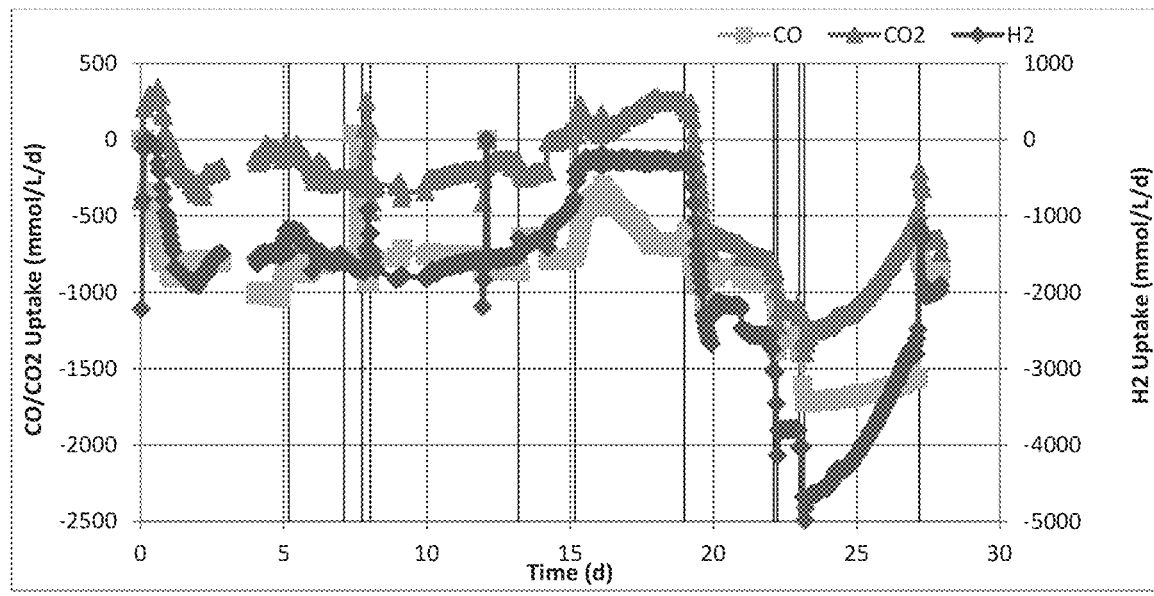
FIG. 4 is a graph showing changes in the uptake of CO, $CO_2$, and $H_2$ by a culture contained in a third reactor in response to changes in the feed gas composition.

FIG. 4 shows the amount of CO, $CO_2$, and $H_2$ consumed by the culture in reactor 4.

In all four reactors, $CO_2$ consumption was demonstrated when the gas feed composition was altered to comprise excess hydrogen. In reactor 3, the amount of $CO_2$ consumed was greater than the amount of CO consumed following reduction of the CO volume in the feed gas. This indicates that $CO_2$ was utilised as the primary carbon source when an excess of $H_2$ is available in the substrate.

Example 2

This example demonstrates that $H_2$ reacts with $CO_2$ over a broad range.

$H_2$, CO, and $CO_2$ consumption by cultures of *Clostridium autoethanogenum* was measured using standard methods. In particular, the flow rates of reactor inlet and outlet gasses were measured using a mass flow controller and the compositions of reactor inlet and outlet gasses were measured using gas chromatography (GC). The rates of consumption of $H_2$, CO and, $CO_2$, expressed in units of mmol/L of broth/day, were calculated from the outlet gas flow. $N_2$ was not consumed by the culture, such that $N_2$ in the inlet gas was equivalent to $N_2$ in the outlet gas. The culture may consume $CO_2$ available in the inlet (feed) gas and/or $CO_2$ produced by the culture.

Figure 5:
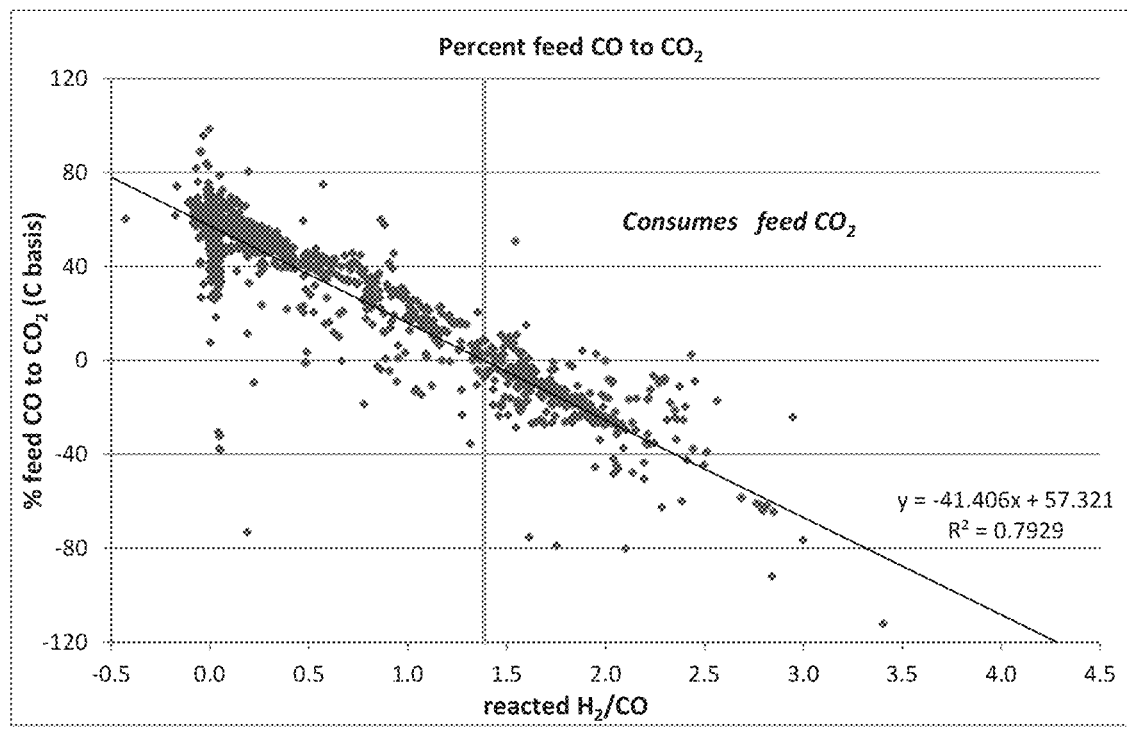
FIG. 5 is a graph showing net consumption of $CO_2$ by a culture.

FIG. 5 shows that $CO_2$ reacted with $H_2$ in a given ratio, and that the culture consumed not only the $CO_2$ produced via CO reaction, but also the $CO_2$ provided in the feed gas, as long as $H_2$ was available. FIG. 5 demonstrates that net consumption of $CO_2$ was achieved. The y-axis of FIG. 5 was calculated by dividing the net consumption (a negative number) or production (a positive number) of $CO_2$ by the consumption of CO (a negative number), and converting the fraction to a percentage value. The x-axis of FIG. 5 was calculated as the fractional ratio of the rate of $H_2$ consumed by the rate of CO consumed.

Example 3

This example demonstrates that increasing the percentage of $H_2$ in a gaseous substrate increases the ratio of ethanol: 2,3-butanediol (BDO) produced by a fermentation culture.

Figure 6:
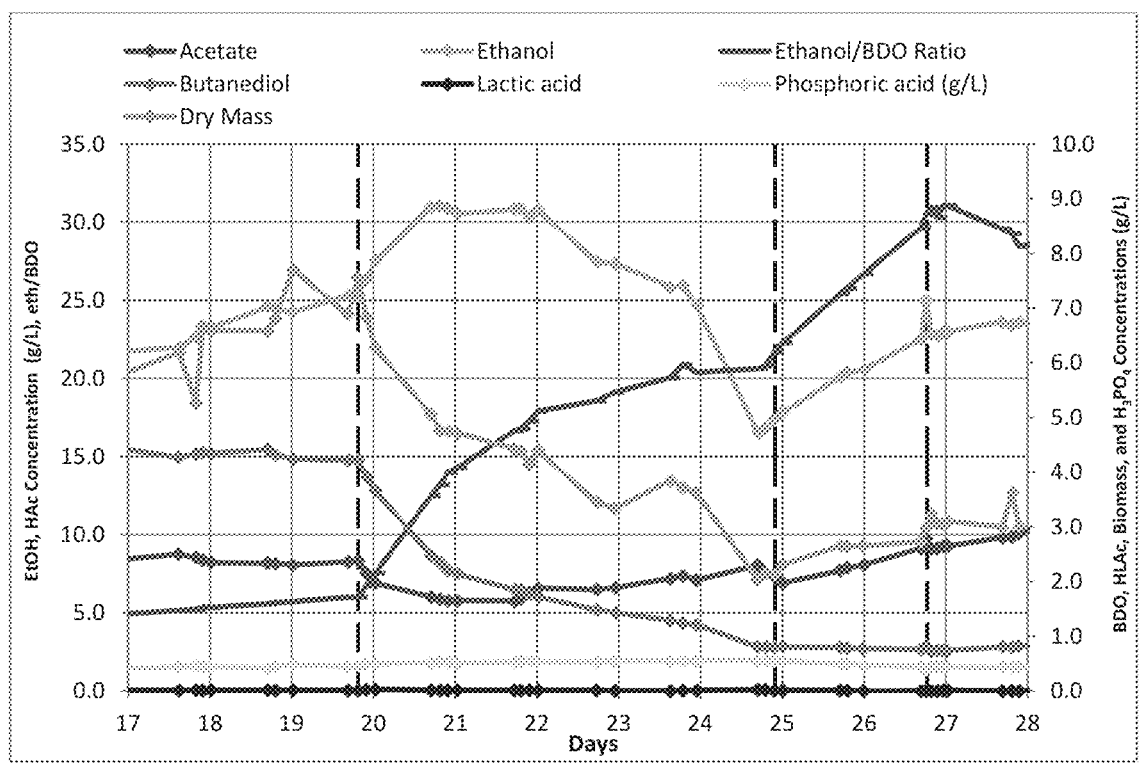
FIG. 6 is a graph showing the metabolic products of a fermentation culture.

FIG. 6 shows the metabolic products of a fermentation culture of *Clostridium autoethanogenum*. At day 20, $H_2$ in the feed gas was increased from 5% to 34% and CO in the feed gas was decreased from 26% to 20%. BDO production dropped from 4.3 g/L to 0.9 g/L and the ratio of ethanol: BDO increased. $H_2$ utilization increased from 15% to 58%. Biomass decreased at a $D_{waste}$ of 0.7.

$H_2$ in the feed gas can be consumed to a large extent (>50%) when CO utilization is high, i.e., when dissolved CO is low. Using an ATP balance, it was predicted that cell growth rate would be slower when $H_2$ was a co-substrate along with CO. It was observed that BDO production rate was decreased as a direct result of the concentration of dissolved $CO_2$ in the broth, and that dissolved $CO_2$ in the broth was linearly related to the $CO_2$ partial pressure (or linearly related to the outlet $CO_2$ concentration at a fixed atmospheric operating pressure), such that the rate of BDO production was inversely related to the consumption of $CO_2$. $D_{waste}$, the residence time of the bacteria in the reactor, can be adjusted to maintain the concentration of bacteria in the reactor at an optimum value. As more $H_2$ is consumed, $D_{waste}$ can be decreased by pumping more broth through the cell membrane.

Example 4

This example demonstrates that the ratio of reacted $H_2$/CO affects product production. In particular, this example demonstrates that biomass and BDO decrease as the ratio of $H_2$:CO in the feed gas increases.

Figure 7:
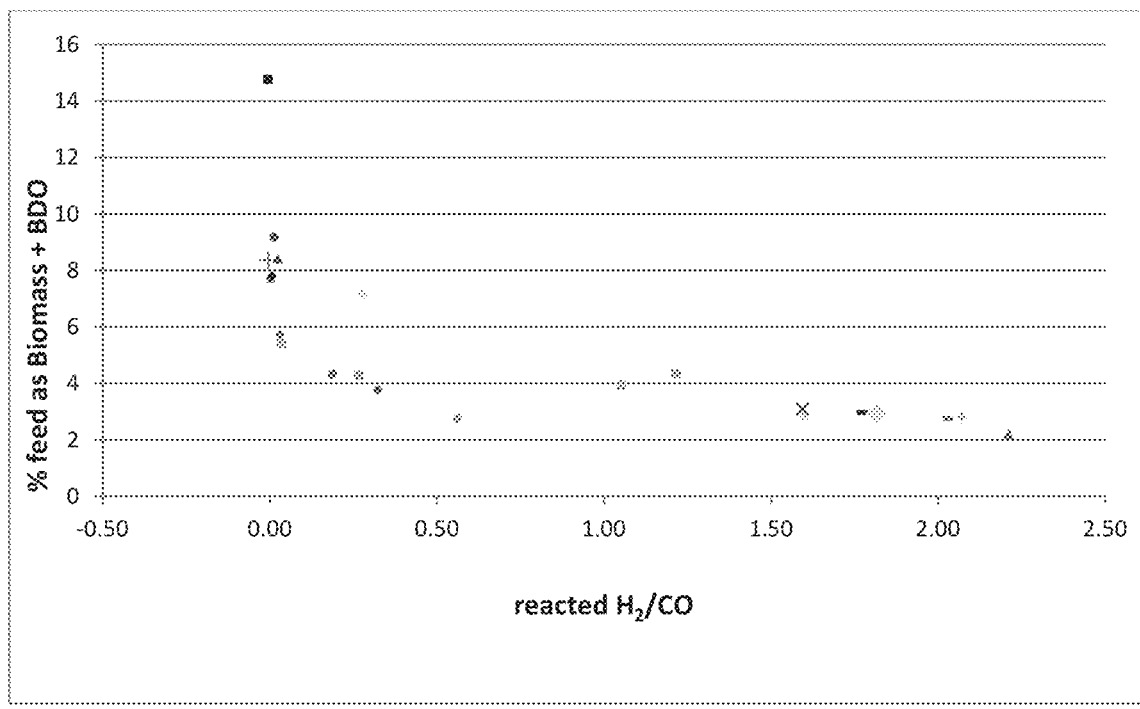
FIG. 7 is a graph showing the effects of the ratio of reacted $H_2$/CO on product production.

FIG. 7 shows data points for a series of experiments similar to the experiment described in Example 3. The y-axis is the ratio of the rate of carbon converted to biomass and BDO to the rate of $H_2$ and CO consumption. If product production was not affected by the $H_2$/CO consumption ratio, then the trend would not decrease with an increase in reacted $H_2$/CO (i.e., a horizontal trend line would be observed).

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A fermentation process comprising:
   a) passing a gaseous substrate stream comprising CO, $H_2$, and $CO_2$ to a bioreactor comprising a carboxydotrophic bacterial culture in a liquid nutrient medium; wherein the ratio of $H_2$:CO in the gaseous substrate stream is at least 3:1 and the ratio of $CO_2$:CO in the gaseous substrate stream is between 1:1 and 4:1;
   b) fermenting the culture wherein at least a portion of the $CO_2$ in the gaseous substrate stream is converted to at least one product selected from alcohols and acids; and
   c) removing the at least one product from the bioreactor, the process characterized in that the specific uptake of $H_2$ by the culture exceeds specific uptake of CO by the culture and the amount of $CO_2$ consumed by the culture exceeds or is equal to the amount of $CO_2$ produced by the culture.

2. The process of claim 1, wherein the gaseous substrate comprises 30-90% $H_2$.

3. The process of claim 1, wherein the at least one product comprises one or more of ethanol, acetate, and 2,3-butanediol.

4. The process of claim 1, wherein the bacterial culture comprises one or more of *Clostridium, Moorella, Oxobacter, Peptostreptococcus, Acetobacterium, Eubacterium,* or *Butyribacterium*.

5. The process of claim 4, wherein the bacterial culture comprises *Clostridium autoethanogenum* or *Clostridium ljungdahlii*.

6. The process of claim 5, wherein the bacterial culture comprises *Clostridium autoethanogenum* deposited under DSMZ accession number DSM23693 or bacteria derived therefrom.

7. The process of claim 1, wherein specific uptake of $H_2$:CO by the culture is at least 1.4:1.

8. The process of claim 1, wherein specific uptake of $CO_2$ by the culture is at least 500 mmol/L/day of $CO_2$.

9. The process of claim 1, wherein the amount of $CO_2$ exiting the reactor is at least 5% lower than an amount of $CO_2$ entering the bioreactor.

10. The process of claim 1, wherein at least 5% of carbon in the at least one product is derived from $CO_2$.

11. The process of claim 1, where specific uptake $H_2$:CO by the culture is at least 2:1.

12. The process of claim 1, wherein the ratio of $H_2$:CO in the gaseous substrate is at least 5:1.

13. The process of claim 1, wherein the gaseous substrate is a pressure swing adsorption (PSA) tail gas.

14. The process of claim 1, further comprising monitoring a mass transfer rate of the gaseous substrate.

15. The process of claim 14, wherein the mass transfer rate of the gaseous substrate is controlled by controlling the partial pressure of the gaseous substrate passed to the bioreactor.

16. The process of claim 1, wherein fermenting the culture is performed at a pressure higher than ambient pressure.

* * * * *